United States Patent [19]

Smith

[11] Patent Number: 4,833,688

[45] Date of Patent: May 23, 1989

[54] TWO-PHASE FLOW QUALITY MEASURING DEVICE

[75] Inventor: William R. Smith, Chattanooga, Tenn.

[73] Assignee: Combustion Engineering, Inc., Windsor, Conn.

[21] Appl. No.: 141,556

[22] Filed: Jan. 7, 1988

[51] Int. Cl.$^4$ .................. G01K 17/12; G01N 25/58
[52] U.S. Cl. ................................. 374/42; 73/29; 374/33; 364/557
[58] Field of Search ............ 374/42, 35; 73/29, 861.04

[56] References Cited

U.S. PATENT DOCUMENTS

| | | | |
|---|---|---|---|
| 3,363,460 | 1/1968 | Baumann | 374/42 |
| 3,413,838 | 12/1968 | Duddy | 73/29 |
| 3,596,516 | 8/1971 | Haynes, Jr. et al. | 374/42 |
| 3,632,210 | 1/1972 | Rich | 73/29 X |
| 3,971,252 | 7/1976 | Onoda . | |
| 4,149,403 | 4/1979 | Muldary et al. | 73/29 |
| 4,455,095 | 6/1984 | Bleiker . | |
| 4,527,600 | 7/1985 | Fisher et al. . | |
| 4,561,785 | 12/1985 | Long et al. | 374/42 |
| 4,576,036 | 3/1986 | Huang et al. . | |

OTHER PUBLICATIONS

ASME Performance Test Codes, Instruments and Apparatus, Part II, Water and Steam in the Power Cycle (Parity and Quality, Leak Detection and Measurement), pp. 81-88, (Date Unknown).
Brochure, "Q: Bar Steam Quality Meter":, EMCO (5 pages), (Date Unknown).

Primary Examiner—Daniel M. Yasich
Attorney, Agent, or Firm—Chilton, Alix & Van Kirk

[57] ABSTRACT

A device and associated method comprising a probe (18) for drawing throttled two-phase steam into a tank (26) which has been evacuated and which can be closed when the pressure of the sample steam in the tank equals the pressure of the source steam mixture (14). The throttling tank operates on the basic thermodynamic principle that a two-phase mixture when throttled into a closed tank becomes superheated. The state of the superheated mixture is determined by temperature and pressure measurements (42, 36). The initial state of the source mixture can then be determined by application of the First Law of Thermodynamics, which is considerably simplified as a result of the way in which the sample is drawn.

9 Claims, 1 Drawing Sheet

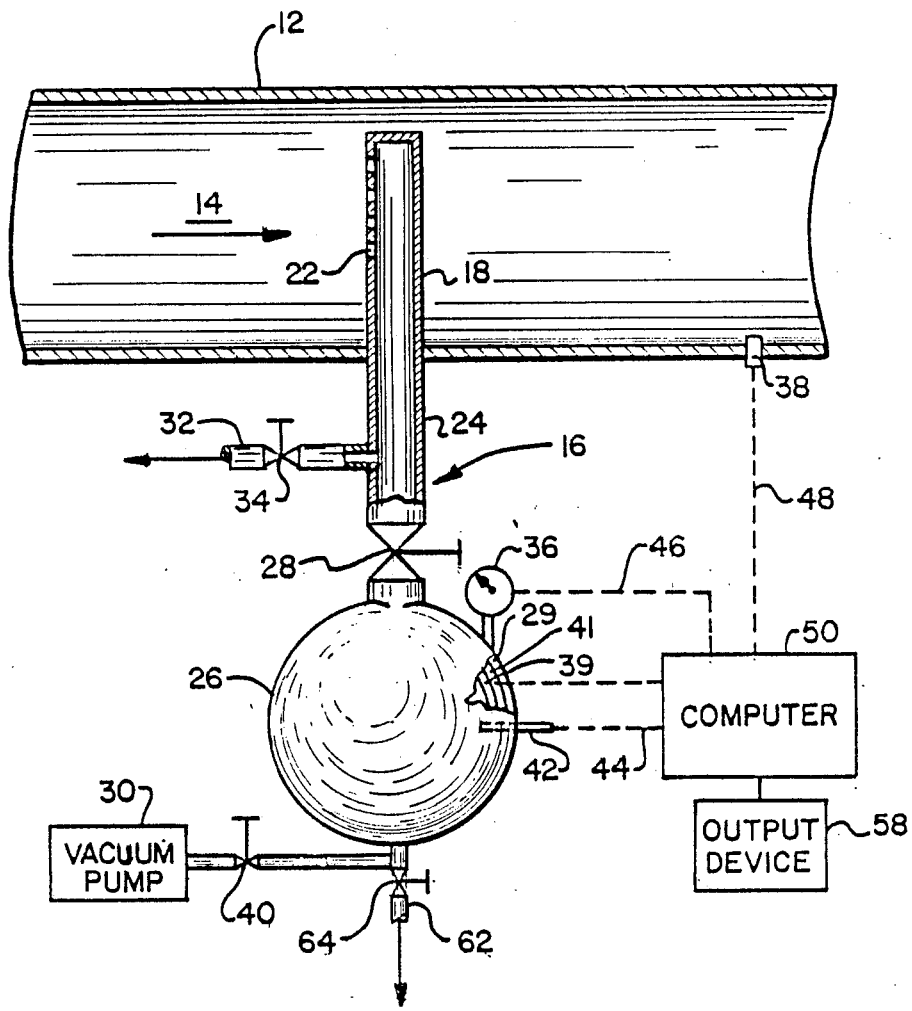

TWO-PHASE FLOW QUALITY MEASURING DEVICE

BACKGROUND OF THE INVENTION

The present invention relates to steam property measuring devices and more particularly, to a device for measuring the quality of steam in a two-phase flow mixture.

The quality of a two-phase flow is a parameter of importance in the operation and design of heat exchangers, turbines, steam engines, pumps and piping systems. In heat exchangers that operate at saturated conditions, such as a steam generator of condenser, the performance is characterized by the state of fluid entering and leaving the heat exchanger. In order to quantify the state of the fluid at saturation conditions, the inlet or exit quality must be known. In a steam generator, for example, lower than expected outlet quality is an indication of poor heat transfer performance of inefficient steam separation equipment. In turbines, high moisture content at the turbine inlet can cause turbine blade erosion as well as reduced system efficiency.

A variety of techniques have been used for measuring the quality of steam. The throttling calorimeter, although in wide use, is subject to a number of constraints and problems. The accuracy is highly dependent on the flow conditions, and the probe is easily clogged with contaminants. The operating fluid is vented to the atmosphere, which makes it undesirable for use in harsh environments, such as nuclear power plants. Furthermore, the throttling calorimeter is not easily adapted for remote operation. Vibrating vane-type quality measuring devices alter the fluid state and thus may yield erroneous results. Techniques using chemical tracers, although reliable, require the addition of chemicals to the working fluid, which is unacceptable in systems that require high purity of the steam. Such techniques are not adaptable to remote operation and typically require several days to complete the chemical sample analysis.

SUMMARY OF THE INVENTION

It is the object of the present invention to provide a two-phase flow quality measuring device that is accurate, is independent of the flow rate of the sampled mixture, has a quick response time and is adaptable for remote operation.

In accordance with the present invention, a throttling tank is arranged and operated on the thermodynamic principle that a two-phase mixture, when throttled into a closed tank, becomes superheated. The state of the superheated mixture can be determined by pressure and temperature measurements. The initial state of the fluid, i.e., the quality, can then be determined by application of the first law of thermodynamics.

In accordance with a method embodiment of the invention, a sample of the mixture is throttled into a closed tank such that the confined sample becomes superheated. The internal energy of the confined sample is determined. The enthalpy of the mixture is then determined from the internal energy of the confined sample, and the quality of the mixture is computed based on its enthalpy.

In a preferred embodiment, the method is accomplished by evacuating a thermally insulated tank and maintaining the evacuated tank at the temperature of the source of the two-phase steam mixture. A throttled mixture sample is drawn into the tank from a source and the tank is closed when the pressure of the steam confined in the tank equals the pressure of the mixture in the source. The sample confined in the tank become superheated and the temperature of the superheated steam is measured. The quality of the steam mixture in the source as a function of the measured temperature of the confined steam and the temperature of the steam mixture is then computed, and preferably displayed or recorded.

In an apparatus embodiment of the invention, the device includes a probe for insertion into the mixture to obtain a throttled supply of sample steam. The probe is fluidly connected to a thermally insulated tank, which can be evacuated and sealed. The probe and tank are arranged so that after the tank is evacuated, a sample of the mixture can be drawn into the tank until the pressure of the sample within in the tank is equal to the pressure of the mixture, at which time the tank is sealed, as by closing isolation valves. A pressure gauge and a temperature sensor are provided in the tank. The temperature and pressure associated with the tank and a temperature of pressure sensor associated with the source of the two-phase mixture are connected to a computer or similar device for looking up or computing the internal energy of the confined sample and the enthalpy of the mixture. This uniquely defines the quality of the mixture.

The present invention can measure the steam quality to a high degree of accuracy, and is relatively insensitive to slight errors in the measured quantities utilized in the computation of the quality. The throttling tank used with the present invention is independent of the flow rate of the mixture in the two-phase source of steam. Because the throttling tank requires only a measurement of temperature and pressure, the response time is almost immediate. The pressure and temperatures can be measured remotely, so that the throttling tank device is easily adapted to remote operation. This is particularly important in hostile environments such as nuclear power plants or chemical plants.

BRIEF DESCRIPTION OF THE DRAWINGS

These and other features of the present invention will be described more fully below with reference to the accompanying drawing in which the FIGURE shows the quality measuring device of the present invention, positioned within a steam source to draw the two-phase steam mixture for measurement of steam quality.

DESCRIPTION OF THE PREFERRED EMBODIMENT

The FIGURE shows a pipe or vessel 12 in which a source of two-phase steam flow 14 is to be measured for quality. As used herein, two-phase flow means a homogeneous flow in a pipe or system consisting of a liquid and a vapor (gas) of the same substance at a uniform saturation temperature. Quality is defined as the ratio of the mass of the vapor flow to the total flow of vapor and liquid. A quality of 0% would be pure liquid, whereas a quality of 100% would be pure vapor.

In accordance with the present invention, a quality measuring device or apparatus 16 includes a sampling probe 18 that is introduced into the two-phase flow 14. The sampling probe 18 preferably includes a perforated portion 22 or other arrangement, whereby the two-phase flow is throttled into the probe. In this context, throttling means causing the mixture to pass through a conduit without developing kinetic energy and while maintaining the total heat constant. An intermediate conduit 24 connects the probe 18 to the tank 26, which is external to the pipe or vessel 12. The tank 26 is preferably insulated 29 to minimize heat transfer through the wall thereof. A tank isolation valve 28 is located in the intermediate conduit 24, by which the flow of the two-phase mixture from the steam source 14 can be controllably introduced into the tank 26.

Before the steam mixture is drawn into the tank 26, a probe drain line 32 and associated valve 34 are utilized to drain the probe while valve 28 is closed. Evacuation pump 30 or the like and associated valve 40 are utilized to evacuate the tank 26. The tank wall 39 is maintained at the temperature of the source steam 14 by heater elements 41 while the tank is under vacuum. Valve 28 is then opened to draw two-phase mixture sample from the pipe 12 into the tank 26. Valve 28 is closed when the tank is full, i.e., when the pressure in the tank, as measured by pressure gauge 36, equals the pressure of the same mixture in the pipe 12 as measured by temperature and/or pressure gauge 38. When the tank 26 is closed, confining the steam sample therein, the temperature of the confined steam is measured with temperature probe 42. Sensor data lines 44, 46 and 48 connect the temperature probe 42, pressure gauge 36 and temperature probe 38, respectfully, to a computer or similar data processing unit 50. As will be described in detail below, the computer 50 determines the quality of the mixture 14 based on the internal energy of the sample confined in the tank 26, which uniquely relates to the enthalpy of the mixture. The results can be displayed or recorded in an output device 58. The probes 42 and 38 provide the data to the computer 50 or controller needed to operate the heater 41 or the like for the tank 26. After completion of the measurement, the tank 26 is emptied through drain line 62 and drain valve 64.

The first law of thermodynamics for a finite time and a uniform state, uniform flow process, can be expressed as follows:

$$Q + m_i(h_i + v_i^2/2 + z_ig) = m_e(h_e + v_e^2/2 + z_eg) + \quad \text{(Eqn. 1)}$$
$$m_2(u_2 + v_2^2/2 + z_2g) - m_1(u_1 + v_1^2/2 + z_1g) + W$$

wherein,
Q is the heat loss from the system
h is the fluid enthalpy
m is the fluid mass
u is the fluid internal energy
v is the velocity of the fluid mass
z is the elevation of the fluid mass, and
W is the work performed by the system
wherein the subscripts have the following meanings:
1—initially in tank
2—final state of fluid in tank
i—state of fluid entering tank from pipe
e—state of fluid leaving tank A number of assumptions can be made regarding the arrangement shown in the drawing, such that Equation (1) can be considerably simplified. For example, the potential and kinetic energies are negligible, so that $z=0$ and $v=0$. No work is done, so that $W=0$, and no mass leaves the tank, so that $m_e=0$. Initially, the tank is evacuated so that $m_1=0$.

Heat loss through the tank 26 to the environment is negligible, but there will be a heat loss from the confined fluid in the tank to the metal wall of the tank as the tank heats up from the initial temperature corresponding to the saturated conditions in the pipe 12 to the superheated temperature of the confined sample. This heat loss Q can be calculated using classical heat transfer theory.

With these assumptions, Equation 1 reduces to the following:

$$Q + m_ih_i = m_2u_2 \quad \text{(Eqn. 2)}$$

Under the further constraint that $m_2 = m_i = m$, the First Law reduces to, $$h_i = u_2 - Q/m \quad \text{(Eqn. 3)}$$

This means that the two-phase enthalpy of the steam mixture 14 in the pipe 12 equals the internal energy of the steam sample in the tank 26, less the heat loss. Two independent physical properties are required to determine the state of a fluid. The pressure and temperature of the fluid in the tank 26 are both known from probes 36 and 42. The internal energy ($u_2$) can be readily determined from steam tables or formulas, or similar look-ups in computer 50 or manually. Similarly, the mass (m) of fluid in the tank can be calculated, and the heat transfer (Q) can be calculated by conventional heat transfer equations.

With quality defined as $X = M_g/M_t$, where $M_g$ is the mass flow rate of vapor and $M_t$ is the total mass flow rate, the quality may be determined from the relation, $$h_i = (1-X)h_f + Xh_g, \quad \text{(Eqn. 4)}$$

where,
$h_f$ = enthalpy of liquid at saturation conditions and
$h_g$ = enthalpy of vapor at saturation conditions
The value of $h_i$ having been determined from Equation (3), the only unknown in Equation (4) is X, the desired quality.

A sensitivity analysis of the effect of a 1° F. error in temperature measurement indicates that, at an operating pressure of 1,000 p.s.i., the variation in quality will be about 0.09%. Since temperature can be measured with much greater accuracy than 1° F., the device in accordance with the invention can measure quality to a significantly greater accuracy than 0.09% for steam at 1,000 p.s.i.a.

An important feature of the invention is that it is not necessary to know the mass flow rate in the pipe 12. Since most of the prior art devices require knowledge of the flow rate, this is an important advantage of the present invention. In addition, other methods such as the throttling calorimeter are designed and calibrated to operated within a specified range of flow conditions. The device of the present invention will operate independently of the flow of steam in the pipe.

I claim:

1. An apparatus for measuring the quality of a two-phase steam source mixture comprising in combination:
   a probe for insertion into the mixture to obtain a throttled supply of sample steam;
   a thermally insulated tank;
   means for initially evacuating the tank;
   means for bringing the tank to the temperature of the steam mixture while the tank is under vacuum;
   means for selectively delivering sample steam at constant enthalpy from the probe to the tank after the tank has been evacuated and brought to the temperature of the sample steam;

means for measuring the pressure in the tank;

means for stopping the delivery of sample steam to the tank when the pressure therein due to the delivery of sample steam is equal to the the pressure of the steam mixture; and means for measuring the sample steam temperature within the tank, whereby the steam quality of the mixture can be computed as dependent on the pressure and temperature of the sample steam as determined from said means for measuring pressure and said means for measuring temperature.

2. The apparatus of claim 1 further including means for computing the enthalpy of the source mixture as a function of the internal energy of the sample steam confined within the closed tank, from the relation, $$h_i = u_2 - Q/m$$

where $h_i$ = enthalpy of mixture
$u_2$ = internal energy of sample steam confined within closed tank
Q = heat loss of confined steam through tank wall
m = mass of confined steam.

3. The apparatus of claim 2 further including means for computing the quality of the mixture from the computation of the enthalpy of the mixture from the relation $$h_i = (1-X)h_f + Xh_g$$

where

X = quality of steam mixture
$h_f$ = enthalpy of liquid at saturation
$h_g$ = enthalpy of vapor at saturation.

4. A method of measuring the quality of a saturated two-phase steam source mixture comprising the steps of:

throttling a sample of the mixture into a closed tank such that the confined sample becomes superheated;

determining the internal energy of the confined sample;

determining the enthalpy of the source mixture from the determination of the internal energy of the confined sample; and computing the quality of the mixture from the determination of the enthalpy of the mixture.

5. The method of claim 4 wherein the determination of the enthalpy of the mixture includes solving the relationship, $$h_i = (1-X)h_f + Xh_g$$ for the quality X, where, $h_i$ is first determined from the relation
$h_i = u_2 - Q/m$ and where,
$h_i$ = enthalpy of mixture
$u_2$ = internal energy of sample steam confined within closed tank
Q = heat loss of confined steam through tank wall
m = mass of confined steam
X = quality of steam mixture
$h_f$ = enthalpy of liquid at saturation
$h_g$ = enthalpy of vapor at saturation.

6. The method of claim 4 wherein the step of throttling a sample of the mixture is preceded by the steps of evacuating the tank and maintaining the evacuated tank at the temperature of the steam source mixture.

7. A method for measuring the quality of a two-phase steam source mixture comprising:

evacuating a tank;

maintaining the evacuated tank at the temperature of the mixture;

drawing a throttled source mixture sample into the tank and closing the tank when the pressure of the steam confined therein equals the pressure of the source mixture;

permitting the temperature of the confined steam and tank to rise due to the energy of the confined steam;

measuring the temperature increase of the confined steam; and computing the quality of the steam mixture as a function of the measured temperature of the confined steam and the temperature of the steam mixture.

8. The method of claim 7 wherein the computation of the quality of the steam is corrected for the heat transferred from the steam sample to the tank wall.

9. The method of claim 8 wherein the computation includes solving the relationship $$h_i = u_2 - Q/m = (1-X)h_f + Xh_g$$

where $h_i$ = enthalpy of mixture
$u_2$ = internal energy of sample steam confined within closed tank
Q = heat loss of confined steam through tank wall
m = mass of confined steam
X = quality of steam mixture
$h_f$ = enthalpy of liquid at saturation
$h_g$ = enthalpy of vapor at saturation.

* * * * *